(12) United States Patent
Hierold et al.

(10) Patent No.: US 10,899,706 B2
(45) Date of Patent: Jan. 26, 2021

(54) METHOD FOR PREPARING METHIONINE

(71) Applicant: Evonik Operations GmbH, Essen (DE)

(72) Inventors: Judith Hierold, Hannover (DE); Daniel Sudhoff, Hanau (DE); Martin Steurenthaler, Bad Vilbel (DE); Hans Joachim Hasselbach, Gelnhausen (DE); Philipp Roth, Hanau (DE); Thorsten Merker, Erftstadt (DE); Markus Held, Limeshain (DE); Daniel Fischer, Midlothian, VA (US); Christian Kaiser, Waldaschaff (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/471,338

(22) PCT Filed: Dec. 15, 2017

(86) PCT No.: PCT/EP2017/082960
§ 371 (c)(1),
(2) Date: Jun. 19, 2019

(87) PCT Pub. No.: WO2018/114640
PCT Pub. Date: Jun. 28, 2018

(65) Prior Publication Data
US 2020/0115334 A1    Apr. 16, 2020

(30) Foreign Application Priority Data
Dec. 21, 2016   (EP) .................................... 16205829

(51) Int. Cl.
*C07C 323/58*    (2006.01)

(52) U.S. Cl.
CPC .................................. *C07C 323/58* (2013.01)

(58) Field of Classification Search
CPC .................................................... C07C 323/58
USPC ......................................................... 558/351
See application file for complete search history.

(56) References Cited

U.S. PATENT DOCUMENTS

| 9,095,161 B2 * | 8/2015 | Kobler ................. C07D 241/08 |
| 2010/0098801 A1 | 4/2010 | Kobler et al. |
| 2013/0008384 A1 | 1/2013 | Kobler et al. |
| 2013/0011514 A1 | 1/2013 | Kobler et al. |
| 2015/0223495 A1 | 8/2015 | Kobler et al. |

FOREIGN PATENT DOCUMENTS

| CN | 102399177 A | 4/2012 |
| JP | 2002-105048 A | 4/2002 |
| WO | WO 2010/043558 A1 | 4/2010 |

OTHER PUBLICATIONS

International Search Report and Written Opinion dated Mar. 15, 2018 in PCT/EP2017/082960 filed Dec. 15, 2017.

* cited by examiner

*Primary Examiner* — Yong L Chu
(74) *Attorney, Agent, or Firm* — Oblon, McClelland, Maier & Neustadt, L.L.P.

(57) ABSTRACT

The present invention relates to a method for preparing methionine or methionine salts. In particular, the invention describes the step of preparing 2-hydroxy-4-(methylthio)butyronitrile (MMP-CN) from 3-methylthiopropanal (MMP) and hydrogen cyanide (HCN) in the presence of ammonia by bringing a gaseous mixture comprising HCN and ammonia into contact with MMP.

20 Claims, 1 Drawing Sheet

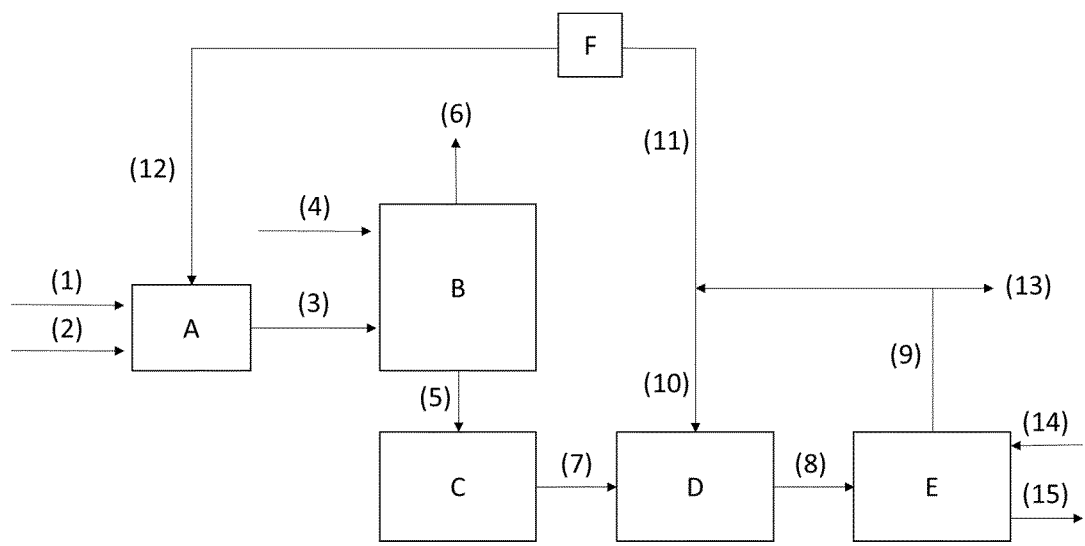

METHOD FOR PREPARING METHIONINE

The present invention relates to a method for preparing methionine or salts thereof. In particular, the invention describes the preparation of 2-hydroxy-4-(methylthio)butyronitrile (MMP-CN) from 3-(methylthio)propanal (=methylmercaptopropionaldehyde, MMP) and ammonia-containing hydrogen cyanide (hydrocyanic acid, HCN).

2-Hydroxy-4-(methylthio)butyronitrile (MMP-CN) is an intermediate, inter alia, in the preparation of methionine. Methionine is an essential amino acid which is used, inter alia, as supplement in feedstuffs. More detailed information can be found in many text books, for example in Ullmann's Encyclopedia of Industrial Chemistry in the chapter entitled "Amino Acids", published online on 15 Apr. 2007, DOI: 10.1002/14356007.a02_057.pub2.

In many common methods, methionine is produced as a racemate, a mixture of the D- and L-enantiomers, in a multi-stage chemical route, for example via the so-called hydantoin route from acrolein, methyl mercaptan, hydrogen cyanide and ammonium carbonate:

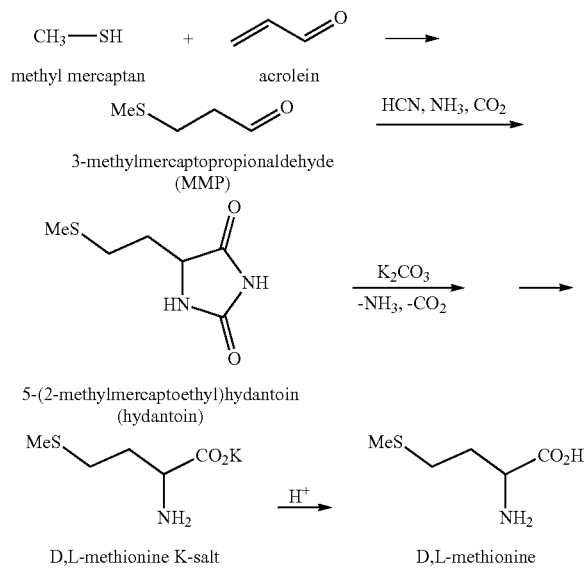

The second step, the synthesis of 5-(2-methylmercaptoethyl)hydantoin (hydantoin), can be carried out directly from MMP, HCN, ammonia and $CO_2$ or alternatively in two stages via the formation of the cyanohydrin precursor MMP-CN:

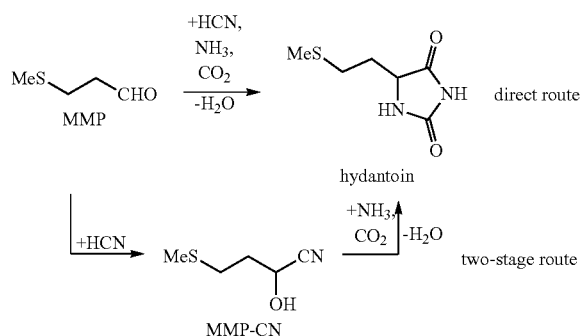

EP 0780370 A2 discloses a method for preparing methionine, in which the MMP, HCN, ammonia and carbon dioxide react to give a methionine precursor, hydantoin (direct synthesis of hydantoin). The molar ratio of ammonia to MMP may be between 1.2 and 6 in this case and the molar ratio of ammonia to carbon dioxide is 1.2 to 4.0. According to this method, MMP is converted to the hydantoin in practically quantitative yield. The hydantoin thus prepared is then further cleaved to form a methionine salt. The ammonia and carbon dioxide formed by the cleavage may be recyclyed into the process. JP 2003104959 A and JP 2003104960 A describe a similar method for reacting MMP with HCN, $NH_3$ and $CO_2$ to give hydantoin. Here, the molar ratios of ammonia to MMP and $CO_2$ to MMP can have values in each case from 1.5 to 2.5.

The earlier applications GB 936664 A and GB 1108926 A also describe a method for reacting MMP with HCN, $NH_3$ and $CO_2$ to give hydantoin by reacting aldehydes or ketones with an equimolar or excess amount of $CO_2$ and an excess of ammonia in aqueous milieu.

WO2012/113664 A1 and WO 2012/113665 A1 describe a method for preparing MMP-CN from MMP and HCN, the first step of the two-stage route to hydantoin mentioned above.

A multiplicity of methods for preparing hydrogen cyanide is described in the literature. The most frequently used in industrial practice are the so-called Andrussow process (DE 102007034715A1 and Chemie-Ing.-Techn., 1953, No. 12, pp. 697-701) and the so-called BMA process (Blausäure [hydrocyanic acid] from Methane and Ammonia, DE1041476 and Chemie-Ing.-Techn., 1958, No. 5, pp. 305-310 [1]). Whereas in the reducing BMA process methane and ammonia are converted to hydrocyanic acid, the oxidizing Andrussow process proceeds from methane, ammonia and oxygen. Both methods are described in more detail in "Handbook of Heterogeneous Catalysis", editor: G. Ertl. et al, second edition, Vol. 5, Chapter 12.3 "Hydrocyanic Acid (HCN) Production" 2592-2609 [2] and in Ullmann's Encyclopedia of Industrial Chemistry, "Cyano Compounds, Inorganic" published online on 15 Oct. 2011, DOI: 10.1002/14356007.a08_159.pub3 [3].

Both the Andrussow and the BMA process proceed with incomplete conversion based on ammonia. The HCN crude gas stream leaving the reactor therefore comprises proportions of ammonia in both cases. The following typical contents of HCN and ammonia (in % by volume) for this gaseous product mixture directly after the HCN production can be found in the literature:

TABLE 1

| Process | HCN (vol %) | $NH_3$ (vol %) | $NH_3$/HCN (mol/mol) | Reference |
|---|---|---|---|---|
| Andrussow | 7.0 | 1.7 | 0.24 | [2] |
| Andrussow | 7.6 | 2.3 | 0.30 | [3] |
| Andrussow | 6.6 | 2.6 | 0.39 | [1] |
| BMA | 22.9 | 2.5 | 0.11 | [3] |

The molar ratio $NH_3$/HCN (mol/mol) presented in Table 1 arises due to Avogadro's Law from the corresponding concentrations of ammonia and hydrocyanic acid in % by volume:

$NH_3$/HCN (mol/mol)=[$NH_3$ (vol %) in the product mixture]/[HCN (vol %) in the product mixture]

CN103408498A discloses in addition the following concentration range for $NH_3$ and HCN in the crude HCN gas stream after the Andrussow process: 1.6±2% by weight $NH_3$ and 8.8±2% by weight HCN. The corresponding molar ratio $NH_3$/HCN can be calculated therefrom to be at maximum 0.84.

The gaseous product mixture directly after the HCN synthesis according to the Andrussow process comprises, in addition to HCN and ammonia, especially water but also methane, nitrogen, hydrogen, CO and $CO_2$ and other constituents. A typical composition of an HCN crude gas stream prepared according to the Andrussow process is: HCN: 7.6% by volume, $NH_3$: 2.3% by volume and $H_2O$: 23.1% by volume [3]. Typical yields in the formation of hydrocyanic acid, based on ammonia, are around 63%.

In the BMA process, the crude HCN gas stream comprises, in addition to HCN and ammonia, especially water but also methane, nitrogen and further constituents. A typical composition of a crude HCN gas stream prepared according to the BMA process is: HCN: 22.9% by volume, $NH_3$: 2.5% by volume and Hz: 71.8% by volume [3]. Typical yields of hydrocyanic acid, based on ammonia, are around 83%.

The crude HCN gas mixture is typically at temperatures of over 1000° C. directly after the preparation in both methods and is immediately cooled. The ammonia present in the crude HCN gas stream is immediately removed in all common processes, by washing with dilute sulfuric acid for example. This is especially necessary to avoid autocatalytic exothermic hydrocyanic acid polymerization which occurs particularly at elevated pH and at phase transitions such as in the liquefaction of HCN.

If pure hydrocyanic acid is required, the crude product, after removing the ammonia, is usually absorbed in cold water to remove the inert gases and at a later stage purified by distillation. The purified hydrocyanic acid may then be used either in gaseous form or, after acid stabilization and condensation, in liquid form in further process steps, for example, in the method for preparing methionine.

According to Chemie-Ing.-Techn., 1953, No. 12, pp. 697-701, around 60% of the ammonia used is converted to hydrocyanic acid in the Andrussow process, 10% is lost via the offgas and 30% is bound as ammonium sulfate in the acid wash with sulfuric acid.

By means of the BMA process, HCN yields of over 80% based on ammonia are achieved, although still at least 10% of the ammonia has to be removed in an acid wash in the process (Chemie-Ing.-Techn., 1958, No. 5, pp. 305-310).

The problems of the unavoidable ammonium sulfate formation resulting from acid washing with sulfuric acid and the loss of $NH_3$ used have long since been known to those skilled in the art and several alternative solutions to this problem have been proposed.

U.S. Pat. No. 2,590,146 A discloses the absorption of the crude HCN gas mixture, prepared according to the Andrussow process, in an aqueous solution of a boric acid-pentaerythritol complex, whereupon ammonia is reversibly chemically bound. The unbound hydrocyanic acid is then separated by distillation, followed by decomposition of the ammonia-boric acid-pentaerythritol complex and separation of the ammonia released. This multi-stage method thus enables the separation of HCN and ammonia from the crude HCN gas mixture.

The principle of reversible binding of ammonia from the crude HCN gas stream is also observed according to U.S. Pat. No. 2,899,274 A. The use of an aqueous solution of saturated fatty acids and ammonium salts thereof as absorption medium for ammonia is described therein.

U.S. Pat. No. 3,112,177 A discloses the use of $CO_2$ in water to reversibly bind ammonia; U.S. Pat. Nos. 2,797,148 A and 3,914,386 A propose ammonium hydrogen phosphate solution for the same purpose.

All these methods are technically very complex; in addition, the reversible absorption and desorption of ammonia is never complete and has to be optionally supplemented with a downstream sulfuric acid wash. Therefore, carrying out the HCN synthesis with subsequent acid washing to form ammonium sulfate remains the most common industrial practice to date. Common to all known methods is the rapid removal of ammonia from the crude HCN gas stream by means of an acidic gas scrubbing.

It would be advantageous if the removal of ammonia and other constituents of the crude HCN gas mixture could be wholly or partly dispensed with. This is not possible however according to the current state of the art. In addition to the aforementioned tendency of liquid hydrocyanic acid to polymerize in the presence of ammonia, ammonia also presents further problems in the subsequent process steps of methionine synthesis. For instance, although carrying out the cyanohydrin synthesis, the reaction of MMP to MMP-CN, in the presence of a base in accordance with U.S. Pat. No. 5,756,803 leads to acceleration of this reaction, at the same time it promotes a more rapid decomposition of the cyanohydrin formed and of the aldehyde used which results in an intensive discolouration of the reaction mixture. In order to circumvent this problem, U.S. Pat. No. 5,756,803 A therefore proposes not using amine in the cyanohydrin formation.

U.S. Pat. No. 2,745,745 mentions the preparation of a cyanohydrin, MMP-CN for example, by means of a catalyzed reaction of MMP with anhydrous liquid hydrocyanic acid. In this case, pyridine or other basic amines can function as catalyst.

WO2012/113664 A1 and WO 2012/113665 A1 describe a further catalytic method for preparing a storage-stable cyanohydrin MMP-CN from MMP and gaseous hydrocyanic acid. In this case, a trilakylamine is used as catalyst. By selecting suitable additives and storage conditions, MMP-CN with high storage stability was obtained. It is pointed out in the description that, after removal of the ammonia from the crude HCN gas mixture by acid washing, further purification steps prior to the MMP-CN synthesis can be omitted.

CN 103408498 A and CN 103420883 A likewise disclose a synthesis of MMP-CN from MMP and non-distilled HCN. In this case, hydrocyanic acid is obtained by the Andrussow process and is freed from ammonia prior to the cyanohydrin synthesis by absorption with sulfuric acid.

JP2002105048 discloses a synthesis of MMP-CN from MMP and HCN catalyzed by ammonia. Pure ammonia-free hydrocyanic acid is mixed as an aqueous solution with MMP. An amine, ammonia for example, is then added to this mixture in catalytic amounts. The amount of catalyst used according to this application can be from 0.001 to 0.05 mol to 1 mol of MMP, the molar ratio of HCN to MMP has the values of 1.0 to 1.1, the possible molar ratio of ammonia to HCN calculated therefrom being from 0.0009 to 0.05.

This list shows that in all known methods the hydrocyanic acid after the preparation is directly freed from ammonia by an acid wash. None of the present publications disclose a synthesis of MMP-cyanohydrin from MMP and gaseous hydrocyanic acid which has not been previously freed from ammonia, or the conversion of MMP-cyanohydrin thus prepared to give methionine or other conversion products.

The object of the present invention is to provide an economical method for preparing MMP-cyanohydrin and conversion products thereof, particularly methionine, from non-purified gaseous hydrocyanic acid in high overall yield and purity.

The primary aim in this case is to minimize the cost and inconvenience of removing ammonia from the crude HCN gas stream and to simplify the method by eliminating the acid wash. This process intensification enables a reduction of the total number of method steps of methionine synthesis. In addition, the formation of ammonium salts is avoided by means of this simplified HCN synthesis and therefore the amount of by-products of methionine synthesis is reduced. Furthermore, the specific requirement for ammonia for methionine production is reduced since the excess ammonia is not removed from the crude HCN gas mixture but is passed into the subsequent process steps.

The technical objects addressed are achieved by a method for preparing 2-hydroxy-4-(methylthio)butyronitrile (MMP-CN), comprising a step B, in which a gas mixture comprising hydrogen cyanide (HCN) and ammonia is brought into contact with 3-methylmercaptopropionaldehyde (MMP) and a product mixture comprising 2-hydroxy-4-(methylthio)butyronitrile (MMP-CN) is thereby obtained.

The invention further provides a method for preparing methionine or a salt of methionine, comprising a step B, in which a gas mixture comprising hydrogen cyanide (HCN) and ammonia is brought into contact with 3-methylmercaptopropionaldehyde (MMP) and a product mixture comprising 2-hydroxy-4-(methylthio)butyronitrile (MMP-CN) is thereby obtained. MMP-CN can then be further reacted to give methionine (salt), for example according to one of the methods from the prior art mentioned above.

In Table 2 below, the chemical names used in the description, abbreviations thereof and their corresponding systematic names according to IUPAC and also the CAS numbers are listed.

TABLE 2

| Name | Abbreviation | IUPAC Name | CAS No. |
|---|---|---|---|
| 3-Methylmercaptopropionaldehyde | MMP | 3-(Methylsulfanyl)propanal | 3268-49-3 |
| 2-Hydroxy-4-(methylthio)butyronitrile | MMP-CN | 2-Hydroxy-4-methylsulfanylbutanenitrile | 17773-41-0 |
| 2-Amino-4-(methylthio)butyronitrile | MMP-AN | 2-Amino-4-(methylsulfanyl)butanenitrile | 3198-47-8 |
| 5-(2-Methylmercaptoethyl)hydantoin | Hydantoin | 5-(2-Methylsulfanylethyl)imidazolidine-2,4-dione | 13253-44-6 |
| | Iminodinitrile | 2,2'-Bis(2-(methylmercaptoethyl)iminodiacetonitrile | 1807317-18-5 |

The invention will be more particularly elucidated below with reference to FIG. 1, which depicts a specific embodiment of the present invention, which embodiment is particularly suitable for preparing a methionine salt. This greatly simplified drawing is intended to give a complete overview of the method steps according to invention. In the following (Table 3), the process steps A to F, the corresponding streams (1) to (15) and the associated mixtures are described in greater detail.

TABLE 3

Reference numbers/letters and explanations of FIG. 1.

| | |
|---|---|
| A | HCN synthesis (according to Andrussow or BMA process) |
| B | MMP-CN synthesis from MMP and crude HCN gas mixture from A |
| C | Optional MMP-CN intermediate storage |
| D | Hydantoin synthesis |
| E | Hydantoin cleavage |

TABLE 3-continued

Reference numbers/letters and explanations of FIG. 1.

| | |
|---|---|
| F | Optional purification of ammonia |
| (1) | Reactant mixture comprising $CH_4$ and $NH_3$ supplied to HCN reactor A |
| (2) | Optional $N_2$ and/or $O_2$ supplied to HCN reactor A |
| (3) | Ammonia-containing crude HCN gas mixture supplied to MMP-CN synthesis B |
| (4) | MMP supplied to MMP-CN synthesis B |
| (5) | MMP-CN mixture supplied to MMP-CN intermediate storage C |
| (6) | Offgas from MMP-CN synthesis B |
| (7) | MMP-CN mixture supplied to hydantoin synthesis D |
| (8) | Mixture comprising hydantoin supplied to hydantoin cleavage E |
| (9) | Mixture comprising $NH_3$, $CO_2$ and $H_2O$ from hydantoin cleavage E |
| (10) | Mixture comprising $NH_3$, $CO_2$ and $H_2O$ supplied to hydantoin synthesis D |
| (11) | Mixture comprising $NH_3$, $CO_2$ and $H_2O$ supplied to further utilization |
| (12) | Mixture comprising $NH_3$ supplied to HCN synthesis A |
| (13) | Mixture comprising $NH_3$, $CO_2$ and $H_2O$ supplied to further utilization and/or disposal |
| (14) | A base |
| (15) | Mixture comprising a methionine salt |

In HCN synthesis A, in the case of the Andrussow process, hydrocyanic acid (HCN) and water is prepared in an exothermic reaction from methane, ammonia (stream (1)) and oxygen (stream (2)). In the case of the BMA process, hydrocyanic acid (HCN) and hydrogen is prepared in an endothermic reaction from methane and ammonia (stream (1)).

The crude HCN gas mixture from HCN synthesis A (3) is brought into contact with MMP (4), preferably in liquid form, in step B. After removal of the gaseous portion of the MMP-CN product mixture, the offgas (6), the liquid portion of the product mixture (5) is optionally intermediately stored in step C. The product mixture comprising MMP-CN from step B, after optional intermediate storage in step C, is transferred as stream (7) to the hydantoin synthesis D and reacted there with ammonia and $CO_2$ or salts thereof to give the hydantoin. In this case, ammonia and $CO_2$ are preferably introduced as stream (10) from the downstream step E. The mixture comprising hydantoin from step D is transferred via stream (8) to step E where the hydantoin is converted to a corresponding methionine salt by action of a base. Here, an appropriate base is fed to step E via stream (14) and the methionine salt is withdrawn from step E via stream (15). The ammonia and carbon dioxide released by the cleavage of hydantoin is withdrawn from step E via stream (9). A portion of this mixture can optionally be routed for disposal as stream (13), a further portion can be recycled to step D and yet another portion can be transferred as stream (11) to an optional purification step F. The ammonia purified to a suitable degree in step F can be recycled to step A or used in some other way.

Step B according to the invention, in which a gas mixture comprising HCN and ammonia is brought into contact with MMP thereby forming a product mixture comprising MMP-CN, may be configured in a different way.

One possible embodiment of step B is absorption of the gaseous mixture comprising HCN and ammonia by liquid MMP. The contacting of a gas mixture comprising HCN and ammonia with liquid MMP may be carried out in an absorption tower or another or two or more apparatuses suitable for the purpose, in which efficient mixing of gaseous and liquid constituents is possible, in which relatively rapid conversion of MMP and HCN to MMP-CN can be achieved. Further possible embodiments of step B include a stirred reactor, a loop reactor or a cascade of such reactors connected in series. In addition, for carrying out step B, besides further apparatuses generally known in the art, the following may also be used: a tray column, a random packing column, a droplet column or a bubble column reactor.

The gas mixture comprising HCN and ammonia and the liquid MMP are preferably brought into contact with each other in countercurrent. If an absorption tower is selected to carry out step B, the gas mixture comprising HCN and ammonia is preferably introduced in the lower section of such an absorption tower, while the liquid MMP is introduced into the upper part of this tower.

In step A preceding step B, hydrogen cyanide may be prepared by the Andrussow process or by the BMA process.

In the oxidizing Andrussow process, a gas mixture essentially comprising HCN, ammonia and water is prepared in an exothermic reaction from methane, ammonia and oxygen. Air is normally used as oxygen source. The product mixture after the HCN synthesis typically additionally comprises other gases such as nitrogen, argon, hydrogen, carbon monoxide, carbon dioxide and methane.

In the BMA process, the gas mixture essentially comprising HCN, ammonia and hydrogen is prepared from methane and ammonia. The product mixture after the HCN synthesis may additionally contain, inter alia, low amounts of nitrogen and methane. Both HCN syntheses described above are typically carried out over platinum-based catalysts.

The essential part of the present invention is the use of gaseous hydrogen cyanide, not freed or only partially freed from ammonia, directly after the preparation thereof. The crude HCN gas mixture is not subjected in this case to an acidic wash, as is customary, but is converted directly in step B according to the present invention, after optional cooling, to a mixture comprising MMP-CN.

The molar ratio of ammonia to HCN in the gas mixture comprising HCN and ammonia, which is reacted in step B, can be from 0.05 to 1.00, preferably from 0.06 to 0.99, preferably from 0.07 to 0.80, particularly preferably from 0.08 to 0.75, especially preferably from 0.10 to 0.70. The molar ratio can be determined here from the gas composition of the gas mixture comprising HCN and ammonia:

$NH_3 / HCN(mol/mol) = [NH_3(mol\%) \text{ in the mixture}] /$ $[HCN(mol\%) \text{ in the mixture}] = [NH_3(\% \text{ by volume}) \text{ in the mixture}] /$ $[HCN(\% \text{ by volume}) \text{ in the mixture}] =$ $[NH_3(\% \text{ by weight}) \text{ in the mixture} \times M(HCN)] /$ $[HCN(\% \text{ by weight}) \text{ in the mixture} \times M(NH_3)],$ where M(HCN)=27.025 g/mol and M(NH$_3$)=17.031 g/mol are the molar masses of HCN and ammonia.

The crude HCN gas mixture, after production according to Andrussow or BMA, is typically at temperatures of >1000° C. and is therefore immediately cooled in order to prevent decomposition of the hydrogen cyanide. This cooling of the HCN-containing gas mixture prior to step B can be conducted, for example, by means of one or more heat exchangers connected in series. In this case, the energy can be withdrawn stepwise or continuously from the crude HCN gas mixture and optionally further used at another point in the process or externally. The temperature of the HCN-containing gas stream directly before step B may be from 0 to 800° C., preferably from 10 to 500° C., particularly preferably from 20 to 300° C. The temperature maintained during the performance of step B may be from 0 to 300° C., preferably from 0 to 100° C., particularly preferably from 0 to 80° C.

The product mixture comprising MMP-CN obtained after step B can be separated into a gaseous mixture and a liquid mixture in and/or after step B. The gaseous mixture (offgas), comprising nitrogen, hydrogen and/or methane, is optionally further purified. It can be used as fuel gas to obtain energy or to obtain individual constituents, hydrogen for example. The liquid mixture, comprising MMP-CN, can be used in subsequent steps as described below.

It has been found, surprisingly, that no polymerization of HCN occurs if the crude HCN gas mixture is brought directly into contact with MMP instead of being washed with acid as customary. Instead, MMP is converted rapidly and virtually completely to a mixture comprising MMP-CN and the corresponding amino derivatives 2-amino-4-(methylthio)butyronitrile (MMP-AN) and 2,2'-bis(2-(methylmercaptoethyl)iminodiacetonitrile (iminodinitrile) as main by-products:

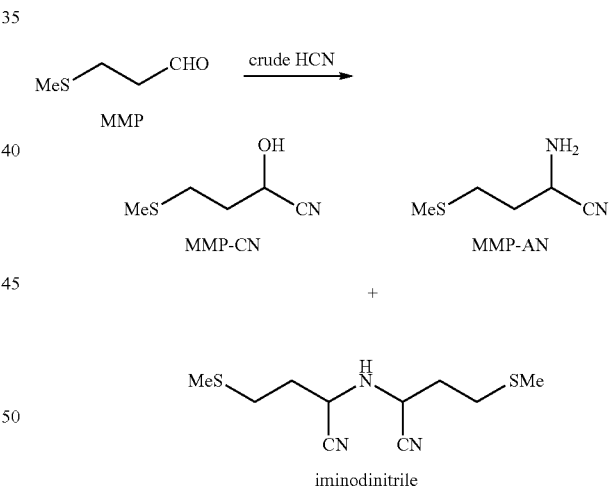

In the method according to the invention, the product mixture obtained in step B therefore comprises, besides MMP-CN, also 2-amino-4-(methylthio)butyronitrile (MMP-AN) and/or 2,2'-bis(2-(methylmercaptoethyl)iminodiacetonitrile (iminodinitrile).

The product mixture from step B can optionally be purified by distillation or in another manner, for example by phase separation, stripping or membrane technology, by removing at least a portion of the water present therein. This step is particularly useful in HCN production by the Andrussow process and may be carried out directly after step B, during the intermediate storage in step C or in the process steps following thereafter. Therefore, the originally biphasic aqueous-organic mixtures after step A according to the Andrussow process with subsequent step B can, if necessary, be made monophasic (organic) and be further processed in a simpler manner. If step A is carried out according to the BMA process, a monophasic mixture is present after step B.

For logistic and process technology reasons, it may be advantageous or necessary not to convert a mixture comprising MMP-CN in further process steps of the methionine synthesis directly after its preparation, but rather time-delayed, after intermediate storage C. It is important in this case that the intermediate product MMP-CN is stable over a relatively long period, i.e. can be stored without considerable decomposition of cyanohydrin. The method according to the invention may therefore further comprise a step C, in which the product mixture obtained in step B is stored at temperatures no higher than 60° C., preferably no higher than 40° C., particularly preferably no higher than 20° C. and a pH of 2 to 8, preferably 4 to 7, before this product mixture is further reacted.

The pH of the product mixture after step B results in particular from the molar ratio of ammonia to hydrogen cyanide used in step B and may vary depending on the HCN process used (Andrussow or BMA) or process parameters.

The pH of the product mixture may also change during step B and C. For instance, the pH may drop, for example, if the conversion of ammonia to MMP-AN and iminodintrile progresses. If an absorption tower is used to carry out step B, a pH gradient may thereby be produced along the absorption tower.

The product mixture comprising MMP-CN, after step B and an optional step C, may be reacted in a step D with ammonia and/or ammonium salts and carbon dioxide and/or carbonic acid salts to give 5-(2-methylmercaptoethyl)hydantoin (hydantoin). This reaction to give the hydantoin can be carried out, for example, in a stirred pressure reactor at elevated temperature. The ammonia and carbon dioxide required for this reaction may be introduced into step D as corresponding gases, singly or as a mixture, optionally with water, or at least partially as the corresponding ammonium carbonate and/or ammonium hydrogen carbonate salts or aqueous solutions thereof. In aqueous solutions, ammonia, carbon dioxide, carbonate ions, hydrogen carbonate ions and ammonium ions are in equilibrium with one another. For simplification, only ammonia and $CO_2$ are mentioned in the further description.

It could be shown that not only MMP-CN but also the main by-products MMP-AN mentioned above and, in a particularly surprising manner, even the relatively stable iminodinitrile, can be successfully reacted to give the hydantoin.

In step E, the hydantoin can be reacted under basic conditions with formation of carbon dioxide and ammonia to give at least one methionine salt. The bases used may be, for example, oxides, hydroxides, carbonates or other salts of the alkali metals or alkaline earth metals, the rare earth metals or ammonium salts and also mixtures of these bases. Particular preference is given to using carbonates or hydrogen carbonates of the alkali metals or ammonium, particularly preferably potassium, sodium or ammonium carbonate or mixtures thereof.

The manner of the ammonia used and partially reused in the method according to the invention plays a particular role. The ammonia and the carbon dioxide from step E according to the invention may be at least partially recycled to step D. By way of preference, only the ammonia and carbon dioxide recycled from step E is used in step D.

The ammonia from step E according to the invention may be at least partially recycled to step A. The ammonia thus recycled may be used there again for HCN production. In this case, the ammonia is preferably freed from sulfur-containing compounds and optionally from $CO_2$ and water before it is recycled to step A.

The ammonia from step E according to the invention may be at least partially disposed of. In this case it is preferably catalytically or non-catalytically incinerated.

The methionine salt obtained in step E may be reacted with an acid in a further process step to give methionine. The method according to the invention for preparing methionine or a salt of methionine may be carried out batchwise or continuously, preferably continuously. The continuous reaction of hydantoin to give methionine via a methionine salt is known in the literature.

In addition to the formation of methionine or methionine salts, the product mixture comprising MMP-CN obtained after steps A and B according to the method according to the invention may also be reacted in further process steps, according to U.S. 20110295006 A1 for example, to give 3,6-bis(2'-methylmercaptoethyl)-2,5-diketopiperazine (DKP) or, according to DE 2261926 A1, to give the dipeptide of methionine, methionylmethionine (Met-Met).

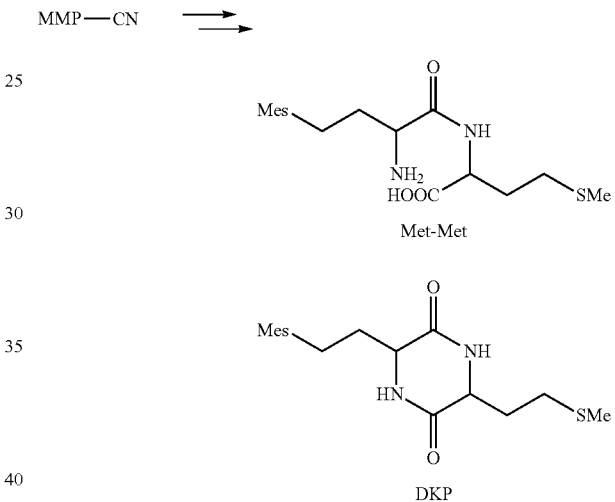

EXAMPLES

Methods Used

Determination of Free Ammonia by Neutralization Titration

The content of physically dissolved ammonia in MMP-CN was determined by means of neutralization titration with hydrochloric acid with potentiometric indication of the equivalence point. For this purpose, ca. 800 mg of the sample as a solution in distilled water (5-10 mL) was initially charged (plastic disposable syringe) and titrated with 0.1 molar hydrochloric acid. The equivalence point was determined by means of pH electrode. The performance of the neutralization titration is known to those skilled in the art.

Determination of Free Hydrocyanic Acid by Means of Titration

The content of free hydrocyanic acid in MMP-CN was determined by means of argentometric back-titration with ammonium thiocyanate using potentiometric indication of the end point (Volhard titration).

For this purpose, 70 mL of 2-propanol/glacial acetic acid mixture (5.715 mL of glacial acetic acid in 2.5 L of 2-propanol), 10 mL of 0.1 molar silver nitrate solution and ca. 4 g of sample were initially charged in a titration vessel, 1 mL of glacial acetic acid was added and the mixture titrated to the end point with 0.1 molar ammonium thiocyanate standard solution. The precise sample weight was determined by differential weighing. The performance of the Volhard titration is known to those skilled in the art.

Determination of Water Content by Karl Fischer Titration

The $H_2O$ content in MMP-CN was determined by the titration method using biamperometric indication of the end point (Karl-Fischer titration).

For this purpose, 20-30 ml of titration medium (e.g. Hydranal Solvent 5 from Fluke), were initially charged in the titration vessel and titrated to dryness with titrant, (e.g. Hydranal Titrant 5 from Fluke). An amount of sample of ca. 500 mg was added to the titrated reservoir (plastic disposable syringe) and titrated with the titrant to the end point. The precise sample weight was determined by differential weighing.

The procedure of this standard method is known to those skilled in the art (see e.g. P. A. Bruttel, R. Schlink: *Wasserbestimmung durch Karl-Fischer-Titration* [*Water determination by Karl-Fischer titration*] Metrohm AG).

High Performance Liquid Chromatography (HPLC)

The majority of the chromatographic investigations (MMP-cyanohydrin, MMP, MMP-aminonitrile, methionine, methionine amide, hydantoin, hydantoin amide, Met-Met, methionine diketopiperazine) were carried out by HPLC from JASCO on an RP-18 column (250×4.6 mm; 5 μm) with subsequent UV detection at 210 nm. A phosphoric acid-acetonitrile-water mixture (3.3 g $H_3PO_4$, 6.8 g acetonitrile, 89.9 g $H_2O$) served as eluent. At a flow rate of 1 mL/min, 10 μL of the respective sample solution (50 mg of sample in 25 mL of $H_2O$) were injected. Calibration was effected in advance by the injection of suitable calibration solutions and evaluated by peak area comparison by means of the external standard method. The procedure of the standard method is known to those skilled in the art.

The iminodinitrile was determined on the HPLC system specified above with identical column, flow rate and detection. In this case, a mixture of methanol and water (each 50% by weight) served as eluent. 10 μL of the respective sample solution (250 mg of sample in 25 mL of eluent) were injected.

Example 1

Preparation of MMP-Cyanohydrin from Ammonia-Containing Hydrocyanic Acid 188 g of 3-methylthiopropionaldehyde (methylmercaptopropionaldehyde, MMP) (94.0% by weight, 1.00 equiv.) from industrial production were metered in at a rate of 6 g/min at the top of a bubble-cap tray column temperature-controlled at 55° C. (5 trays, double jacketed) equipped with reflux condenser. At the bottom of the column by the countercurrent principle, a gas mixture was introduced consisting of hydrocyanic acid (47.0 g, 1.02 equiv. based on MMP, 90 g/h), ammonia (7.99 g, 0.28 equiv. based on MMP, 15.3 g/h), steam (80 g, 156 g/h) and nitrogen (230 NL, 450 NL/h) ($NH_3$:HCN=0.27 mol/mol). The product was collected in a flask fixed to the bottom of the column and analyzed after completion of the MMP addition (ca. 30 min). A clear, colourless biphasic product was obtained. HPLC analysis revealed a total content of 145 g of MMP-cyanohydrin (MMP-CN, 65.1% based on MMP used), 33.8 g of MMP-aminonitrile (MMP-AN, 15.3% based on MMP used) and 30.6 g of iminodinitrile (14.8% based on MMP used). MMP-CN, MMP-AN and iminodinitrile are further referred to as MMP-CN equivalents.

Comparative Example 1

188 g of 3-methylthiopropionaldehyde (methylmercaptopropionaldehyde, MMP) (94.0% by weight, 1.00 equiv.) from industrial production were metered in at a rate of 6 g/min at the top of a bubble-cap tray column temperature-controlled at 55° C. (5 trays, double jacketed) equipped with reflux condenser. At the bottom of the column by the countercurrent principle, hydrocyanic acid (47.0 g, 1.02 equiv. based on MMP, 90 g/h) and nitrogen (230 NL, 450 NL/h) were introduced. The product was collected in a flask fixed to the bottom of the column and analyzed after completion of the MMP addition (ca. 30 min). HPLC analysis of the clear, colourless reaction product (224.0 g) revealed an MMP-cyanohydrin content of 95.4% by weight (96.1% based on MMP used).

Example 2

Stability Studies of MMP-Cyanohydrin from Ammonia-Containing Hydrocyanic Acid

In a three-necked flask cooled in an ice bath, equipped with jacketed coil condenser and thermometer, 79.0 g of 3-methylthiopropionaldehyde (96.3% by weight, 1.0 equiv.) from industrial production were stirred magnetically. A gas mixture consisting of 20.8 g of hydrocyanic acid (1.05 equiv.) and 2.12 g of ammonia (0.17 equiv.) was introduced ($NH_3$:HCN=0.16 mol/mol), the addition rate being regulated in this case such that the temperature in the reaction vessel never exceeded 40° C. On completion of addition, the mixture was stirred at room temperature for 15 min. The colourless substance obtained was divided among three Schott flasks and stored at 10° C., room temperature or 60° C. for 10 weeks. The results of the analysis after 1 day, 1 week and 10 weeks are summarized in Table 4 below.

TABLE 4

| Storage temperature | Storage period | HPLC [% by weight] | | | Titration [% by weight] | | |
| --- | --- | --- | --- | --- | --- | --- | --- |
| | | MMP-CN | MMP-AN | Dinitrile | $H_2O$ | $NH_3$ | HCN |
| 10° C. | 1 day | 67.3 | 7.6 | 13.3 | 5.61 | 0.01 | 0.82 |
| | 1 week | 59.7 | 2.0 | 23.6 | 6.21 | 0.01 | 0.77 |
| | 10 weeks | 60.3 | 0.8 | 25.9 | 6.66 | 0.06 | 1.21 |
| RT | 1 day | 59.5 | 2.2 | 23.0 | 6.18 | 0.02 | 0.75 |
| | 1 week | 58.0 | 1.1 | 25.6 | 6.17 | 0.01 | 1.12 |
| | 10 weeks | 52.9 | 0.9 | 28.7 | 6.36 | 0.08 | 1.42 |
| 60° C. | 1 day | 58.6 | 1.0 | 26.4 | 5.48 | 0.03 | 0.72 |
| | 1 week | 53.8 | 0.7 | 27.3 | 4.97 | 0.01 | 1.22 |
| | 10 weeks | 52.1 | 0.0 | 28.5 | 4.99 | 0.08 | 1.56 |

The results of Example 2 summarized in Table 4 show that the MMP-CN-containing product mixture obtained according to the invention may be kept over a long period (at least up to 10 weeks) at temperatures up to 60° C. and therefore can be used for the subsequent methionine preparation steps.

Example 3

Preparation of Hydantoin from MMP-Cyanohydrin Prepared with Ammoniacal Hydrocyanic Acid In a 300 mL autoclave beaker equipped with a stirrer bar, distilled water (52.0 g), ammonium carbonate (11.9 g) and ammonium hydrogen carbonate (30.2 g) were added to 35.0 g of MMP-cyanohydrin prepared with ammoniacal hydrocyanic acid ($NH_3$:HCN=0.17 mol/mol), consisting of 60.1% by weight MMP-CN, 3.7% by weight MMP-AN and 20.9% by weight iminodinitrile. The reaction vessel was transferred to a high-pressure laboratory autoclave from ROTH, equipped with manometer, heater, temperature sensor and pressure release. The autoclave was tightly sealed, heated with stirring at 105° C. over a period of 15 min and then maintained at this temperature for a further 20 min. At the end of the reaction period, the autoclave was cooled to room temperature under running water and the resulting pressure (ca. 17 bar) was vented. HPLC analysis of the reaction product (121.3 g) revealed a content of 24.8% by weight hydantoin (74.9% yield based on MMP-CN equivalents used) and 6.5% by weight hydantoin amide (17.9% yield based on MMP-CN equivalents used).

Comparative Example 3

A comparative experiment for preparing hydantoin analogous to Example 3 but using MMP-cyanohydrin prepared from ammonia-free hydrocyanic acid (35.0 g, 88% by weight) gave 104.7 g of reaction product with a composition of 27.9% by weight hydantoin (71.4% yield based on MMP-CN used) and 8.2% by weight hydantoin amide (19.1% yield based on MMP-CN used).

Example 4

Preparation of Methionine from MMP-Cyanohydrin Prepared with Ammoniacal Hydrocyanic Acid In a 300 mL autoclave beaker equipped with a stirrer bar, distilled water (39.0 g), ammonium carbonate (13.9 g) and ammonium hydrogen carbonate (23.4 g) were added to 35.0 g of MMP-cyanohydrin prepared with ammoniacal hydrocyanic acid ($NH_3$:HCN=0.17 mol/mol), consisting of 64.5% by weight MMP-CN, 4.6% by weight MMP-AN and 19.7% by weight iminodinitrile. The reaction vessel was transferred to a high-pressure laboratory autoclave from ROTH, equipped with manometer, heater, temperature sensor, inlet tube and pressure release. The autoclave was tightly sealed, heated with stirring at 105° C. over a period of 15 min and then maintained at this temperature for a further 20 min. At the end of the reaction period, the autoclave was cooled to 70° C. in a water bath and the resulting pressure (ca. 15 bar) was vented. 40 g of aqueous KOH solution (15 g of KOH in 25 g of $H_2O$) was then metered in via the inlet tube over a period of 10 min. After the addition was complete, the autoclave was heated with stirring at 180° C. over a period of 25 min and then maintained at this temperature for a further 30 min. During the reaction course, the pressure was vented to 5 bar around every 5 min, but at least in the case of 10 bar being exceeded. At the end of the reaction period, the autoclave was cooled to room temperature under running water and depressurized to standard pressure. HPLC analysis of the reaction product (118.8 g) revealed a content of 16.6% by weight methionine (54.8% yield based on MMP equivalents used), 0.7% by weight methionine amide (2.3% yield based on MMP equivalents used), 7.1% by weight methionylmethionine (24.9% yield based on MMP-CN equivalents used) and 0.4% by weight methionine diketopiperazine (1.6% yield based on MMP-CN equivalents used).

Comparative Example 4

A comparative experiment with MMP-cyanohydrin (35.0 g, 95.4% by weight) prepared from ammonia-free hydrocyanic acid gave 142.2 g of reaction product with a composition of 15.1% by weight methionine (56.5% yield based on MMP equivalents used), 1.1% by weight methionine amide (4.1% yield based on MMP-CN equivalents used), 6.2% by weight methionylmethionine (24.7% yield based on MMP-CN equivalents used) and 0.6% by weight methionine diketopiperazine (2.6% yield based on MMP-CN equivalents used).

TABLE 5

Comparison of the preparation of MMP-CN, hydantoin and methionine from ammonia-free vs. ammonia-containing hydrocyanic acid:

| | Yield, % | | |
|---|---|---|---|
| | MMP-CN (MMP-AN; iminodinitrile) | Hydantoin (Hydantoin amide) | Methionine (Met-amide; Met-Met; Diketopiperazine) |
| Example 1 | 65.1 (15.3; 14.8) | | |
| Comparative Example 1 | 96.1 | | |
| Example 3 | | 74.9 (17.9) | |
| Comparative Example 3 | | 71.4 (19.1) | |
| Example 4 | | | 54.8 (2.3; 24.9; 1.6) |
| Comparative Example 4 | | | 56.5 (4.1; 24.7; 2.6) |

The results summarized in Table 5 show that the preparation of the intermediate hydantoin and also of the end product methionine from MMP-cyanohydrin from ammonia-containing (Examples 3, 4) and ammonia-free hydrocyanic acid (Comparative Examples 3, 4) afford comparable yields and spectra of by-products.

The invention claimed is:

1. A method for preparing 2-hydroxy-4-(methylthio)butyronitrile, the method comprising:
   bringing a gas mixture comprising hydrogen cyanide and ammonia into contact with 3-methylmercaptopropionaldehyde, thereby producing a product mixture comprising 2-hydroxy-4-(methylthio)butyronitrile.

2. A method for preparing methionine or a salt of methionine, the method comprising:
   bringing a gas mixture comprising hydrogen cyanide and ammonia into contact with 3-methylmercaptopropionaldehyde, thereby producing a product mixture comprising 2-hydroxy-4-(methylthio)butyronitrile.

3. The method of claim 1, in which a molar ratio of ammonia to hydrogen cyanide in the gas mixture is from 0.06 to 0.99.

4. The method of claim 1, further comprising, prior to the bringing:

preparing the gas mixture essentially comprising hydrogen cyanide, ammonia, and water according to an Andrussow process from methane, ammonia, and oxygen.

5. The method of claim 1, further comprising, prior to the bringing:
preparing the gas mixture essentially comprising hydrogen cyanide, ammonia, and hydrogen according to a BMA process from methane and ammonia.

6. The method of claim 1, further comprising:
separating the product mixture obtained after the bringing in and/or after the bringing into an offgas comprising nitrogen, hydrogen, and/or methane, and a liquid mixture comprising 2-hydroxy-4-(methylthio)butyronitrile, and
optionally purifying the offgas.

7. The method of claim 1, wherein the product mixture obtained in the bringing further comprises 2-amino-4-(methylthio)butyronitrile and/or 2,2'-bis(2-(methylmercaptoethyl)iminodiacetonitrile.

8. The method of claim 2, further comprising:
storing the product mixture obtained in the bringing at temperatures no higher than 60° C. and a pH of 2 to 8, before the product mixture is further reacted.

9. The method of claim 2, further comprising:
first reacting the product mixture obtained in the bringing with ammonia and/or ammonium salts and carbon dioxide and/or carbonic acid salts to give 5-(2-methylmercaptoethyl)hydantoin.

10. The method of claim 9, further comprising:
second reacting the 5-(2-methylmercaptoethyl)hydantoin under basic conditions, thereby forming carbon dioxide and ammonia, to give at least one methionine salt.

11. The method of claim 10, further comprising:
at least partially recycling the ammonia and the carbon dioxide from the second reacting to the first reacting.

12. The method of claim 10, further comprising:
at least partially recycling the ammonia obtained in the second reacting to the preparing.

13. The method of claim 10, further comprising:
at least partially disposing of the ammonia obtained in the second reacting.

14. The method of claim 2, further comprising:
purifying the product mixture from the bringing by distillation by removing at least a part of water.

15. The method of claim 12, further comprising:
freeing the ammonia obtained after the second reacting from sulfur-containing compounds and optionally from $CO_2$ before it is recycled to the preparing.

16. The method of claim 10, further comprising:
reacting the at least one methionine salt with an acid to give methionine.

17. A method for preparing a dipeptide of methionine, the method comprising:
carrying out the method of claim 1, and then, in any order, aminating and hydrolyzing the 2-hydroxy-4-(methylthio)butyronitrile with acid or base to obtain a carboxylic acid;
optionally esterifying the carboxylic acid, to obtain an ester; and
condensing the carboxylic acid and/or the ester to form the dipeptide.

18. A method for preparing 3,6-bis(2'-methylmercaptoethyl)-2,5-diketopiperazine, the method comprising:
carrying out the method of claim 1, and then, in any order, aminating and hydrolyzing the 2-hydroxy-4-(methylthio)butyronitrile with acid or base to obtain a carboxylic acid;
optionally esterifying the carboxylic acid, to obtain an ester; and
condensing the carboxylic acid and/or the ester to form the 3,6-bis(2'-methylmercaptoethyl)-2,5-diketopiperazine.

19. The method of claim 2, in which a molar ratio of ammonia to hydrogen cyanide in the gas mixture is from 0.06 to 0.99.

20. The method of claim 2, further comprising, prior to the bringing:
preparing the gas mixture essentially comprising hydrogen cyanide, ammonia, and water according to an Andrussow process from methane, ammonia, and oxygen.

* * * * *